United States Patent
Utterberg et al.

[11] Patent Number: 6,165,149
[45] Date of Patent: *Dec. 26, 2000

[54] REUSABLE BLOOD LINES

[75] Inventors: David S. Utterberg, Seattle, Wash.;
Neil J. Sheehan, Palo Alto, Calif.

[73] Assignee: DSU Medical Corporation, Las Vegas, Nev.

[*] Notice: This patent issued on a continued prosecution application filed under 37 CFR 1.53(d), and is subject to the twenty year patent term provisions of 35 U.S.C. 154(a)(2).

[21] Appl. No.: 08/892,685

[22] Filed: Jul. 14, 1997

Related U.S. Application Data

[62] Division of application No. 08/504,457, Jul. 20, 1995, Pat. No. 5,772,624.

[51] Int. Cl.[7] .................................................. A61M 37/00
[52] U.S. Cl. .................. 604/5.01; 604/6.16; 604/905; 210/646; 285/333
[58] Field of Search .................................. 604/4–6, 905; 210/646; 285/333, 331, 332

[56] References Cited

U.S. PATENT DOCUMENTS

| | | |
|---|---|---|
| 3,753,493 | 8/1973 | Mellor . |
| 3,861,388 | 1/1975 | Vaughn . |
| 3,871,913 | 3/1975 | Shaldon . |
| 3,992,301 | 11/1976 | Shippey et al. . |
| 3,994,293 | 11/1976 | Ferro . |
| 4,158,034 | 6/1979 | Riede et al. . |
| 4,197,848 | 4/1980 | Garrett et al. . |
| 4,361,485 | 11/1982 | Boonstra . |
| 4,399,030 | 8/1983 | Hlavinka et al. . |
| 4,447,230 | 5/1984 | Gula et al. . |
| 4,493,705 | 1/1985 | Gordon et al. . |
| 4,559,043 | 12/1985 | Whitehouse et al. . |
| 4,612,170 | 9/1986 | Luther et al. . |
| 4,654,026 | 3/1987 | Underwood . |
| 4,658,915 | 4/1987 | Goris et al. ............................ 285/333 |
| 4,673,506 | 6/1987 | Henne et al. . |
| 4,695,385 | 9/1987 | Boag . |
| 4,752,292 | 6/1988 | Lopez et al. . |
| 4,826,477 | 5/1989 | Adams ........................................ 604/4 |
| 4,867,739 | 9/1989 | Kawano ...................................... 604/4 |
| 4,871,353 | 10/1989 | Thomsen . |
| 4,966,585 | 10/1990 | Gangemi . |
| 4,976,685 | 12/1990 | Block, Jr. . |
| 4,981,469 | 1/1991 | Whitehouse et al. . |
| 5,061,365 | 10/1991 | Utterberg . |
| 5,071,413 | 12/1991 | Utterberg . |
| 5,078,699 | 1/1992 | Haber et al. . |
| 5,139,483 | 8/1992 | Ryan . |
| 5,139,675 | 8/1992 | Arnold et al. . |

(List continued on next page.)

FOREIGN PATENT DOCUMENTS

| | | |
|---|---|---|
| 0 090 093 | 12/1982 | European Pat. Off. . |
| 0 256 640 | 6/1987 | European Pat. Off. . |
| 0 442 310 A1 | 1/1991 | European Pat. Off. . |
| 2 021 418 | 5/1979 | United Kingdom . |

*Primary Examiner*—Dennis Ruhl
*Attorney, Agent, or Firm*—Garrettson Ellis; Seyfarth, Shaw

[57] ABSTRACT

Blood lines for hemodialysis and other blood handling procedures may be reused by placing connectors intermediately along the length of the blood lines so that the lines can be disconnected to separate out reusable portions thereof. Specifically, the bulk of the blood lines used may comprise branchless lengths of tubing which are easily reusable, and may be cleaned and stored along with a dialyzer or similar device by connection to a conventional reuse machine. Also, the connectors on the blood lines which are reused may have first and second sealing surfaces. The first sealing surfaces are used in the connections made to form the blood line in its normal form for use. Then, during cleaning and sterilization for reuse, the reusable connectors can connect first and second lengths of blood lines together making use of a second sealing surface, in which the first sealing surfaces are exposed to cleaning/storing solution to cause cleaning and antibacterial action on the first sealing surfaces.

31 Claims, 9 Drawing Sheets

U.S. PATENT DOCUMENTS

| | | |
|---|---|---|
| 5,203,771 | 4/1993 | Melker et al. . |
| 5,224,932 | 7/1993 | Lappas . |
| 5,242,392 | 9/1993 | Vaughn . |
| 5,256,371 | 10/1993 | Pippert . |
| 5,268,144 | 12/1993 | Heilmann et al. . |
| 5,330,425 | 7/1994 | Utterberg . |
| 5,344,568 | 9/1994 | Kitaevich et al. ............................ 604/4 |
| 5,360,395 | 11/1994 | Utterberg ..................................... 604/4 |
| 5,456,676 | 10/1995 | Nelson et al. ............................ 604/283 |
| 5,484,397 | 1/1996 | Twardowski ................................. 604/4 |
| 5,490,925 | 2/1996 | Eigendorf . |
| 5,549,554 | 8/1996 | Miraki . |
| 5,589,070 | 12/1996 | Maltais et al. . |
| 5,591,344 | 1/1997 | Kenley et al. . |
| 5,603,902 | 2/1997 | Maltais et al. . |
| 5,651,893 | 7/1997 | Kenley et al. . |
| 5,693,008 | 12/1997 | Brugger et al. ............................. 604/4 |

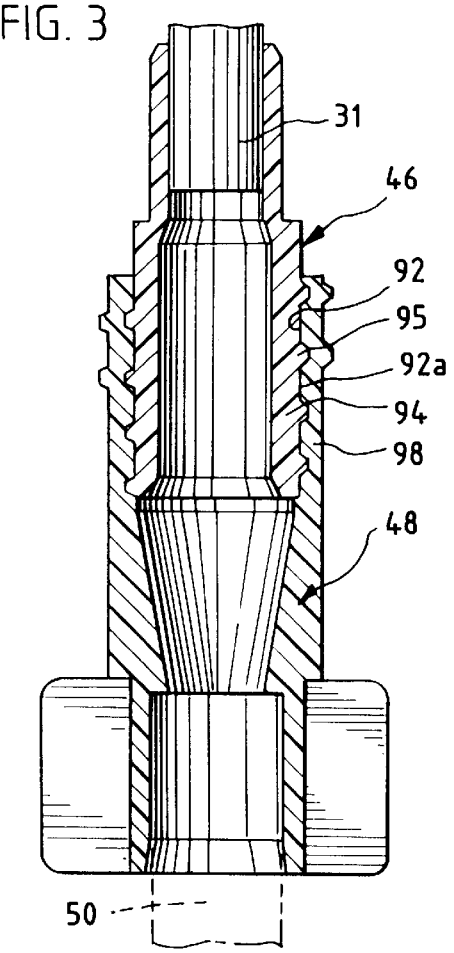
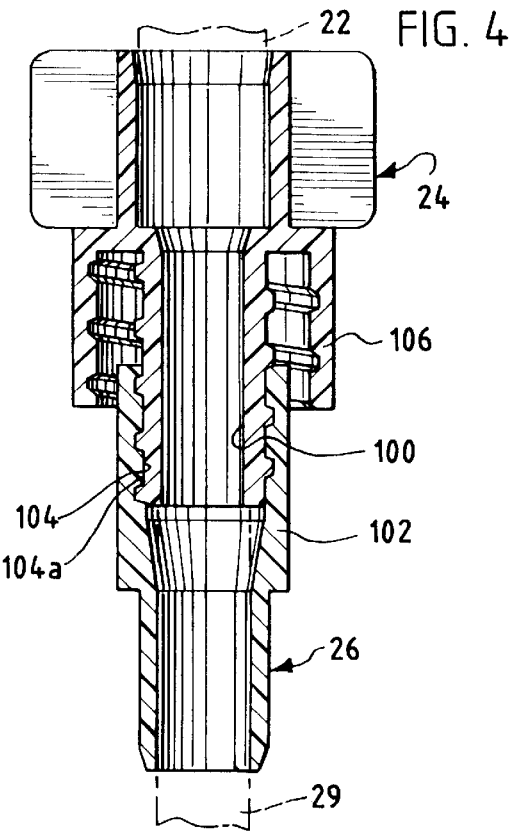
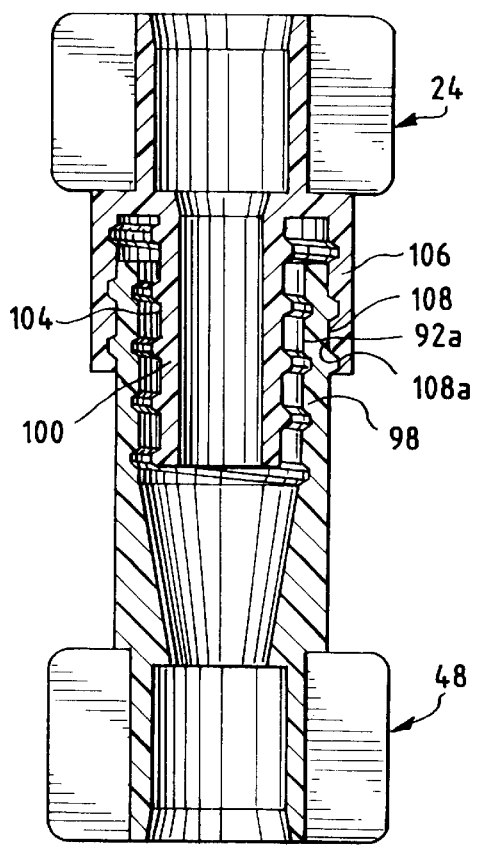

REUSABLE BLOOD LINES

This is a division of application Ser. No. 08/504,457, filed Jul. 20, 1995 now U.S. Pat. No. 5,772,624.

BACKGROUND OF THE INVENTION

In the field of blood treatment, hemodialysis is the most widely used technique, although other techniques are also available such as plasmapheresis, hemoperfusion, blood oxygenation, and techniques for passing blood through blood treatment media such as an absorptive agent for the removal of toxins or the like. Typically, an arterial blood set delivers blood from the patient to the hemodialyzer or other desired blood treatment unit. After the blood has passed through the hemodialyzer, it is conveyed through a venous blood set back to the patient.

The arterial and venous blood sets typically each have about two meters of tubing, extending from patient connectors to other set components such as bubble removal chambers, a length of roller pump tubing or another pump device fitment, branch connection sites, a pressure pillow, and the like. Also, typically another meter of tubing extends between these various other set components and the dialyzer or other blood treatment device. Numerous other known devices may also be positioned on the blood sets, such as filters.

In the early days of dialysis, blood lines and dialyzers were hand-assembled before dialysis, and then disassembled, piece-by-piece, after dialysis for cleaning and resterilization. These early dialyzers were of the plate dialyzer form, and, generally, everything was reused except for the dialyzing membranes. Typically, glass chambers and various metallic fittings were press fit into latex blood tubing, with these components being reused a large number of times.

Since such a process was very expensive in terms of labor cost and time consumption, plastic, presterilized dialyzers and blood lines were introduced in the late 1960's. Initially, these items were disposed of after a single use. However, in due course, the dialyzers particularly began to be reused, always on the same patient and typically for only four to six uses. In countries with less government funding and/or lower cost of labor the reuse of dialyzers, bloodlines, and even fistula needles has been and still is common, despite safety issues.

When U.S. government funding of dialysis began in the mid 1970's, dialyzer reuse substantially disappeared. However, since another funding change in 1982, U.S. dialyzer reuse has been once again increasing.

Particularly, hollow fiber dialyzers have been reused, especially since the introduction of noncellulosic membranes such as polysulphone, which are more capable of exposure to oxidizing agents such as more concentrated liquid bleach, so that at the present time most hemodialyzers are reused, with the reuse typically being done with semi-automated equipment that controls the rinsing, bleach and antiseptic solution application, and other aspects of the disinfection process. Typically, in the more recent reuse techniques, the dialyzer is first disconnected from the arterial and venous blood sets, which are thrown away. Hollow fiber dialyzers have their headers removed in some cases so that the fiber manifolds can be swabbed and cleaned. Then, the dialyzers are connected by short reuse tubes which join its blood inlet, outlet, and dialysate ports to the respective ports on the reuse equipment. The blood and dialysate pathways are sequentially rinsed, followed by application of a bleach solution and another water rinse, following which the dialyzer is filled with a disinfectant solution. The dialyzer is then separated from the short reuse connecting tubes capped, and then stored until the patient's next dialysis. Dialyses are typically performed on a patient three times a week.

Immediately prior to the next use, the dialyzer is typically connected to a new arterial set that has been previously primed with sterile, physiological saline. Then a venous set is attached. The system is rinsed with sterile physiologic saline solution for essential elimination of the disinfectant.

Commonly, blood lines of the arterial and venous sets have not been reused, partly because the cost of blood lines is less than the cost of dialyzers, and also because blood lines are more difficult to reuse than dialyzers. This is because, contrary to the typical hollow fiber dialyzers, traditional blood lines have numerous branch lines, dead end spaces, and enlarged spaces such as are found in the bubble removal chambers and pressure pillows. Thus, efficient, effective cleaning of traditional arterial and venous sets is difficult or impossible.

Also, conventional arterial and venous sets are more difficult to set up for dialysis reuse than typical hollow fiber dialyzers, since the above mentioned components also cause difficulties in the removal of the chemical sterilant prior to reuse. The presence of filters, as are commonly found in the venous sets, presents a major obstacle to effective cleaning prior to reuse. Likewise, arterial and venous sets tend to be long and cumbersome after they have been unwound, making it difficult to manipulate the set during reuse, storage, and setup.

Additionally, unlike dialyzers, certain components of the prior art blood lines are subjected to repeated mechanical force which, as they are made from materials which degrade with use, and thus are not ideal for reuse. This also raises safety issues. For example, the roller pump tubing segment typically carried by blood sets can quickly suffer from a deterioration in elasticity, since the pump segment tubing is crushed and reexpanded thousands of times by the action of the roller pump. The functioning of the pump segment tubing depends upon its elastic "spring back" capability. With a loss of some of that characteristic to spring back from the crushing provided by the roller pump, the amount of blood pumped per rotation of the roller pump rotor decreases. To make matters worse, this can go unnoticed as blood flow rates are typically calculated indirectly in the blood pump by a measurement of the rotational speed of the pump rotor, so that the flow rate may decrease even though the pump rotor speed is maintained. This can take place in part because plasticizers of the typically PVC roller pump segment may have leached out or otherwise because of characteristics of the materials used.

Also, a worn pump segment or diaphragm may shed into the pumped blood excessive amounts of particles from the plastic of which the segment is made.

Also, blood filters and transducer protector filters are reused only with difficulty and inefficiency, because the blood tends to clog the openings of the respective filters. Likewise injection sites may quickly wear out due to repeated punctures and the loss of elasticity as a consequence of use in a dialysis procedure. Organic material that collects in the puncture sites of elastomeric injection site partitions is especially difficult to remove and decontaminate.

Currently, arterial and venous sets for dialysis are reused in some clinics. However, in such reused sets the arterial blood line is generally not equipped with an arterial chamber, which prevents accurate monitoring of arterial pre-pump or post-pump pressures, raising a significant safety issue. Likewise, venous blood lines that are reused generally do not include a filter, which raises another significant safety issue. Furthermore, the reusable arterial and venous blood lines generally lack injection sites and other branch lines, which creates a significant inconvenience and a safety issue.

The reason for these deficiencies in the above reusable blood lines lies in the difficulty of reusing blood lines which have chambers, filters, injection sites, dead end side ports, and branch lines.

Luther et al. U.S. Pat. No. 4,612,170 discloses a blood oxygenator which has a removable and reusable heat exchanger. The remainder of the oxygenator and the blood lines are apparently not intended not to be reused.

Also, the Medisystems Corporation offered for sale during the 1970's and 1980's a neonatal venous line for dialysis in which a central chamber with filter was removably connected at both ends to lengths of tubing which each carried a branching connector site. The purpose of this was to permit replacement of the filter in case the filter became severely clotted during dialysis, to which neonatal dialysis is sometimes prone. It is not believed that any suggestion was made about reuse of any of the components of the neonatal venous line.

DESCRIPTION OF THE INVENTION

By this invention, a blood treatment method is provided, which is typically a hemodialysis technique but may comprise other blood treatment methods as well. The method comprises the following steps:

One flows blood sequentially through connected members which comprise a first conduit; a first blood handling member comprising at least one of a first debubbling chamber and a pump device fitment; a second conduit; a blood treatment device such as a membrane dialyzer; a third conduit; a second blood handling member comprising at least one of a second debubbling chamber and pump device fitment; and a fourth conduit. In a preferred embodiment, the blood treatment device is a hemodialyzer. Typically, blood is withdrawn from the patient into the first conduit, and returned to the patient through the fourth conduit. The conduits are typically flexible plastic tubes of the arterial and venous blood sets, although rigid materials and/or nontubular shaped conduits can preferably be employed in certain circumstance such as cassetted devices or conduits that are permanent or semi-permanent attachments to the treatment device or monitoring/supply device.

Following such treatment, one terminates the flowing of blood and substantially removes the blood from the above components.

In accordance with this invention, at least one of the first and second blood handling members is disconnected from the respective flexible tubes and removed. One then connects ends of at least one of the first and second conduits and/or the third and fourth conduits together, to recreate a blood flow path with the absence of at least one the first and second blood handling members. At least one of the first and fourth conduits are then connected at a free end to a source of cleaning/storage solution, which may sequentially or otherwise include water for rinsing, bleach, and a disinfecting solution used for storage of the blood lines, either with the blood lines being connected to the blood treatment device (hemodialyzer) or separate therefrom if desired. One then flows the cleaning/storage solution through the first through fourth conduits and, optionally, the blood treatment device which in that circumstance is not disconnected from the tubes.

Prior to such connection, the ends of the first, second, third and fourth conduits are preferably treated with an antimicrobial agent such as liquid bleach, following which, the first and second, and the third and fourth, conduits may be connected, thus reducing the risk of microbial contamination.

It is preferred that the above blood treatment method is performed a plurality of times, for example a dozen or more times, with at least some of the same first through fourth conduits. This can save 65 percent or more of conventional, fully disposable plastic of the blood line sets (by weight) in each dialysis procedure, since the first through the fourth conduits may comprise the longest portions of the respective arterial and venous sets. Such a reuse, if universally used in all current United States dialysis procedures, could reduce the consumption of plastic up to four million kilograms per year, which must now be both paid for and then disposed of as biologically hazardous material.

It should also be added that, particularly in the situation where the blood lines remain connected to the dialyzer during cleaning and storage for reuse, the reuse of the first through fourth conduits can be accomplished at an extremely low increased cost compared to the reuse of the membrane dialyzer by itself. The reuse cycle with a conventional reuse machine can be practically the same whether the dialyzer is connected to the reuse equipment alone, or with attached long tube assemblies comprising the first through fourth conduits. Preferably, these long conduit assemblies are free of branch lines, dead end spaces associated with branch lines and other components, and other features that inhibit their reuse.

If desired, either or both of the second and third conduits may be permanently connected to the dialyzer.

Also, the performance standards of the first through fourth conduits on reuse can remain high through a dozen reuses or more, providing performance that is substantially equivalent to the original equipment specifications. It is generally preferred, to enhance reuse capability, that the first, second, third, and fourth (first through fourth) conduits are tubes made of a plastic which is substantially free of plasticizers, or at least leachable plasticizers. For example, polyurethane, silicone, polycarbonate and similar materials may be used. Also, thermoplastic elastomer materials may be used such as Kraton, sold by The Shell Chemical Company.

Typically, with each reuse of the first through fourth conduits, new first and second blood handling members may be respectively connected between the first and second, and the third and fourth, conduits. Priming solution may be passed through the connected conduits blood handling members, and blood treatment device (dialyzer), followed by flowing blood sequentially therethrough in accordance with the original method described above.

Further in accordance with this invention, an arterial or venous set for blood handling is provided, usable in the above method. The set comprises of a first typically flexible tube having ends which respectively carry a first connector (typically a dialyzer connector) and a second connector. A central assembly comprises a pathway conduit having at least one of a blood degassing chamber, a connected branch tube, a pump device fitment, and an injection site. The central assembly carries a third connector which is connected with the second connector, and a fourth connector.

A second typically flexible tube is also provided to the set, having ends which respectively carry a fifth connector and a sixth connector (typically a patient access connector). The fifth connector is connected to the fourth connector of the central assembly. At least the second and fifth connectors are of the type which permit repeated connection and disconnection to permit repeated, sealed blood flow through the set while the connectors are connected, so that they may be reused time after time, while the central assembly may be replaced.

The first flexible tube may correspond exactly to the previously discussed second or third conduits. The second flexible tube may correspond exactly to the first or fourth conduits, depending on usage.

Also, it is preferred for at least the second connector and the fifth connector to define first sealing surfaces that respectively sealingly abut against other sealing surfaces of the third and fourth connectors, to which they are respectively connected. The second and fifth connectors also have second sealing surfaces, the latter two connectors being also connectable with each other to form a sealed connection by contact of the second sealing surfaces while the first sealing surfaces are positioned in exposed manner within the connected second and fifth connectors. This latter condition is accomplished after the central assembly has been removed, and the first and second tubes are connected together for cleaning and reuse. The second sealing surfaces form a sealed connection between the second and fifth connectors by sealing contact together, while the first sealing surfaces in this condition are positioned in exposed manner within the connected second and fifth connectors, so that antimicrobial solution in the joined first and second flexible tubes can be in contact with the first sealing surfaces. Thus, upon desired reuse of the first and second tubes, they may be connected again with the third and fourth connectors of a new central assembly under aseptic conditions since the first sealing surfaces have been cleaned and rendered aseptic.

The second and fifth connectors may each define a threaded sleeve of differing diameter compared with the other sleeve, to permit telescoping, threaded interengagement for a locking connection while the second sealing surfaces are in sealing abutment.

Also, the threaded sleeve of at least one of the second and fifth connectors may be threaded both inside and out to provide engagement between the second and fifth connectors, and also to alternatively provide engagement with the connectors of the central assembly.

Alternatively, an O-ring connector system may be used in which at least one O-ring comprises at least one first or second sealing surface.

Further in accordance with this invention, a flow through blood treatment device and a connected blood set portion comprises a housing, a blood inlet, a blood outlet, and at least one membrane in the housing. The housing defines a blood flow path between the blood inlet and outlet on one side of the membrane, and a second flow path defined on the other side of the membrane. The blood inlet and the blood outlet are each respectively connected to lengths of first blood flow tubing by first connectors positioned at one end of each of the respective lengths of first blood flow tubing, which connectors may provide permanent connection if desired.

The first blood flow tubing carries on its other end a second connector which is connected to a fifth connector (similar to that previously described) carried on one end of a second blood tube. Each length of the second blood tube is connected to a sixth connector, typically a patient access connector, on its end opposed to the end which carries the fifth connector. Thus, a blood treatment device such as a dialyzer may be connected to one or both of the arterial and venous blood sets, in which each of the inlet and outlet tubing assemblies comprises first and second lengths of tubing which are removable one from the other by disengagement of the respective connectors.

Such an arrangement may be cleaned and stored for reuse. Then, when reuse is desired, the respective lengths of first and second tubings can be disconnected, a central assembly containing, for example one or more blood degassing chambers and/or a blood pumping device such as roller pump tubing, may be connected between the respective first and second tubes so that the blood treatment device becomes ready for use.

The respective arterial and venous sixth connectors on the free ends of the second tubes may be connected to each other so that the flow path of the blood treatment device is formed into a closed loop, for storage purposes. Alternatively, the respective sixth connectors may be connected to opposed ends of a short shunt tube or an overconnector for the same purpose.

Particularly, the second and fifth connectors of the above device may have the design previously described, where the connectors define first and second sealing surfaces and where the second and fifth connectors are connectable with each other, with abutment together of the second sealing surfaces while the first sealing surfaces are positioned in exposed manner within the connectors, so that the first sealing surfaces may be cleaned and rendered aseptic for subsequent sealing contact with a sealing surface of another connector.

Because the long first through fourth tubes may be reused many times, they may be made of larger inner cross-sectional area at a very small cost increase, especially when factored over the many separate dialyses in which they are used. Larger inner cross-sectional areas, for example about 0.17 to 0.4 $cm^2$, can desirably reduce the flow pressure drop, which is particularly of advantage in the higher flows of modern dialysis procedures.

Preferably, new first and second blood handling members may be incorporated into the blood treatment device which is to be reused after the antimicrobial agent has been completely removed from the system and replaced with normal saline solution. Thus, setup can be fast and efficient, because the greater part of the blood sets are already primed.

DESCRIPTION OF DRAWINGS

FIGS. 3 and 4 are enlarged, detailed longitudinal sectional views illustrating embodiments of joined connectors as used in FIG. 1;

FIG. 5 is an enlarged longitudinal sectional view illustrating two of the connectors of FIGS. 3 and 4 joined together as shown in FIG. 2;

DESCRIPTION OF SPECIFIC EMBODIMENTS

Figure 1:
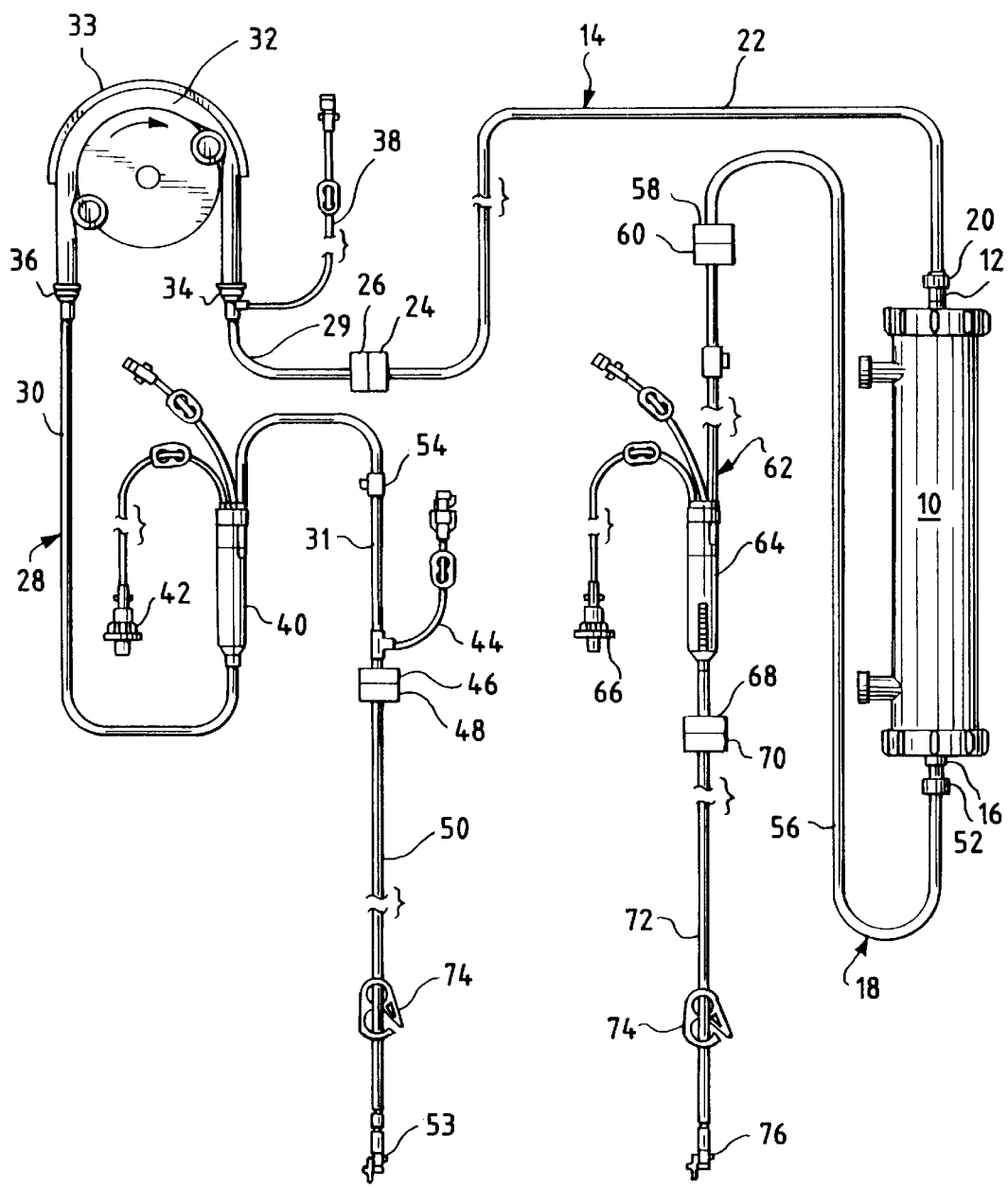
FIG. 1 is plan view of a connected dialyzer, arterial blood set, and venous blood set in accordance with this invention.

Referring to FIG. 1, the blood flow portions of a hemodialysis system are shown. A conventional hemodialyzer 10 has a blood inlet 12 which is connected by a conventional luer lock system to first connector 20 at an end of arterial blood set 14. Dialyzer 10 also has a blood outlet 16, which is connected to a first connector 52 of venous set 18. These sets 14, 18 and dialyzer 10 are of conventional design except as otherwise indicated herein in accordance with this invention.

First connector 20 is carried by first branchless, flexible tube 22 of arterial set 14, which first tube terminates in second connector 24. Second connector 24 communicates with a third connector 26, which is carried by central assembly 28 of arterial set 14. While first flexible tube 22 is preferably without branches or other components except for approximately 100 cm. of plastic tubing, (preferably having an inner diameter of 4.5 to 7 mm. or a lumen cross-sectional area of 0.17 to 0.38 cm$^2$) central assembly 28 may comprise a substantial number of branching and other components carried with tubing segments 29, 30 and 31. A length of roller pump tubing 32 is provided, shown to be in a roller pump track 33 and being retained in line by a pair of pump tubing connectors 34, 36, designed to accommodate the differing diameters of the respective lines. Connector 34 may have a branch connecting line 38 which comprises an anti-backup heparin line, as an optional feature. Between tubings 30, 31 a debubbling chamber 40 may be provided having conventional branch or side arm lines, one of such lines carrying a transducer protector 42 for conventional pressure measurements. At line 31, another conventional branch line 44 may be provided for connection with a source of physiological saline solution. Other designs of central assembly 28 may also be used.

Central assembly 28 terminates in a fourth connector 46, which communicates with fifth connector 48 of a second length of flexible tubing 50, comprising a single, unbranched tubing length of about 180 cm. length, and having a lumen cross section typically similar to first flexible tube 22.

Finally, arterial set 14 may be terminated with a conventional sixth connector 53 of luer lock type.

If desired, components may be added or subtracted to the arterial and venous sets shown. For example, an injection site 54 of conventional design may be placed on the arterial set in the position shown, or any other desirable position, including on reusable tubing conduits 14, 50, 72, or 18.

A significant difference in the arterial set 14 of this invention over the prior art arterial sets lies in the presence and design of connectors 24, 26, and 46, 48. Arterial set 14 may be used in a conventional dialysis procedure. Then, at the end of the procedure, after the blood has been substantially rinsed from set 14, connectors 24 and 26, and connectors 46, 48 may be respectively disconnected, and central assembly 28 may be removed. Then, connectors 24 and 48 may be connected together in the manner to be shown below. Preferably, the mode of connection between connectors 24 and 48 is different from the mode of connection between connectors 24, 26 and 46, 48, so that the first sealing surfaces utilized in sealing contact between the respective connectors 24, 26 and 46, 48 are open and exposed within the connected connectors 24, 28, so that the application of cleaning/storage solution through the set causes cleaning and antibacterial action on these first sealing surfaces.

Venous blood set 18 also comprises a first connector 52, which connects to or is integral with the blood outlet of dialyzer 10, and is carried by a first length of tubing 56, which may be about 80 cm long and is preferably free of branches in a manner similar to the previously described first tubing 22.

First tubing 56 terminates at its other end to second connector 58 which, in turn, communicates with a third connector 60 carried by the central assembly 62 of this blood set 18. Central assembly 62 comprises a filter-carrying debubbling chamber 64 and preferably branch lines as desired, one of said branch lines carrying a transducer protector 66 in a manner similar to the previous arterial set 14.

Central assembly 62 also carries a fourth connector 68 which is in sealed, connected relation to a fifth connector 70 which is carried upon second length of tubing 72. Second length of tubing 72 is similar in length and diameter to the other second tubing 50, being also preferably free of branch connections, pressure pillows, injection sites, and other chambers. On-off clamps 74 are preferably externally carried on the tubings adjacent the respective connectors, and are not deemed an integral feature thereof.

Second tubing 72 of the venous set 18 terminates in a conventional sixth connector 76 of the luer lock type, for patient access connection.

Here also, at the termination of dialysis and the removal of all possible blood from the system, connectors 58, 60 and 68 and 70 may be disconnected, and the preferably specially designed connectors 58, 70 may be connected to each other, preferably in a manner as described above where the original sealing surfaces providing the sealed connection between connectors 58, 60 and 68, 70 are exposed to the connectors' interior for washing and contact with the cleaning/storage solution in preparation for reuse.

Thus, first and second tubings 22, 50, 56, 72, comprising in this embodiment about eighteen feet of tubing, can be reused in an indefinite number of dialysis procedures, resulting in substantial savings of plastic and reduced problems of the disposal of biohazard waste. With each use, it is typically contemplated that new central assemblies 28, 62 are connected into the respective sets between the respective first and second tubes 22, 50, 56, 72, but if necessary and as possible, central assemblies 28, 62 may be cleaned and rehabilitated for reuse also.

Figure 2:
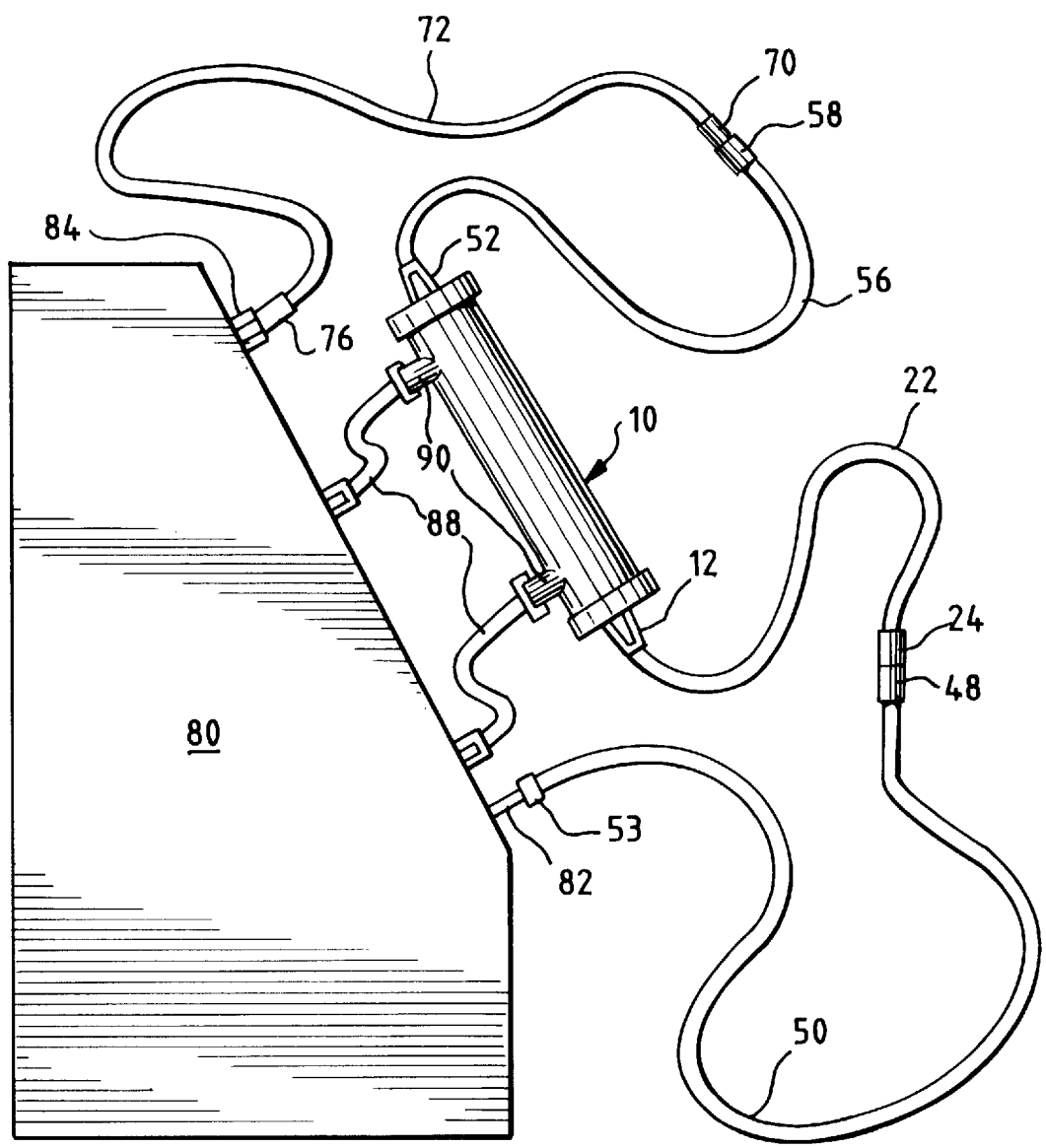
FIG. 2 is a generally schematic elevational view showing the dialyzer and blood sets of FIG. 1 connected to a reuse machine for cleansing of the system for later reuse, with certain set components removed.

FIG. 2 shows the set of this invention after disconnection of the central assemblies 28, 62, and reconnection of the respective long tubes 22, 50, 56, 72, with the dialyzer 10, and the connected long tubes and dialyzer being mounted on a conventional reuse machine 80. Sixth patient connectors 53, 76 of each set may be connected to special reuse connectors 82, 84 which hold connectors 53, 76 in sealed relation to provide cleaning/storage solution to the system with their first sealing surfaces exposed to the solution so that the surfaces are cleaned. As is conventional, short tubes 88 from reuse machine 80 connect to the dialysis ports 90 of dialyzer 10, so that cleaning/storage solution, typically a sequence of various types of washing, sterilizing and storage solutions, are applied to the dialyzer and the tubular set components.

If desired, after such washing, connectors 53, 76, may be connected together using an interconnector or an overconnector; the dialysis ports 90 may be closed; and the dialyzer and connected tubing may be removed from reuse machine 80 for storage until the next desired use.

At least some of the connectors used in this invention define first sealing surfaces that seal with one type of connector, and second sealing surfaces which seal with another type of connector in such a manner that the first sealing surfaces are positioned in exposed manner within the connectors so that antimicrobial solution in the joined connectors can be in contact with the first sealing surfaces. This later condition corresponds with the situation in FIG. 2, so that the first sealing surfaces can be exposed to the antimicrobial effect of the cleaning agents of reuse machine 80 or any reuse program desired. Thus, when new central assemblies 28, 62 are provided, the first sealing surfaces are placed back into sealing operation and do so under aseptic conditions, having been cleaned and subjected to antimicrobial action.

In illustration of this, FIG. 3 is an enlarged, longitudinal sectional view of connectors 46, 48 of arterial set 14, showing the connection and the first sealing surface 92 which is generally circular in cross section and formed with screw threads 95 on male portion 94 of connector 46, in sealing relation with first sealing surface 92a on female portion 98 of connector 48.

FIG. 4 shows another design of connector system of the arterial set, namely connectors 24 and 26 in their connected relationship. Threaded male sleeve 100 of connector 24 is in screw-threaded engagement with female sleeve 102 of connector 26, providing a first sealing surface 104 on male sleeve 100 and in sealing relation with female sleeve 102 at its first sealing surface 104a. Connector 24 also carries an outer sleeve 106 with inner threads, for use in its second connection.

The corresponding connectors of venous set 18 may be of similar design.

Referring to FIG. 5, this shows the situation when central assembly 28 is removed from arterial set 14, and connectors 24, 48 are connected together as illustrated in FIG. 2. Sleeve 98 of connector 48, threaded both inside and out, is capable of receiving outer sleeve 106 of connector 24 in threaded relation as shown in FIG. 5. In this configuration, the outer surface 104 of sleeve 100 of connector 24 is inwardly spaced from the inner surface of sleeve 98, so that the first sealing surfaces 92a, 104 of the respective connectors are open and accessible to the antimicrobial cleaning/storage solution that is provided in the configuration of FIG. 2 for cleaning of those surfaces 92a, 104. The remaining connectors 46, 26 are respectively connected to central assemblies 28, 62, which are removed, and do not participate in the process of this invention any further. Annular, second sealing surfaces 108, 108a are provided between the inner surface of outer sleeve 106 and the outer surface of sleeve 98, as shown.

Thus, upon reuse of arterial set 14, when a new, sterile central assembly 28 is provided, one can be confident that the new first sealing surfaces 92a, 104 formed with new connectors 26, 46 will be aseptic.

Figure 6:
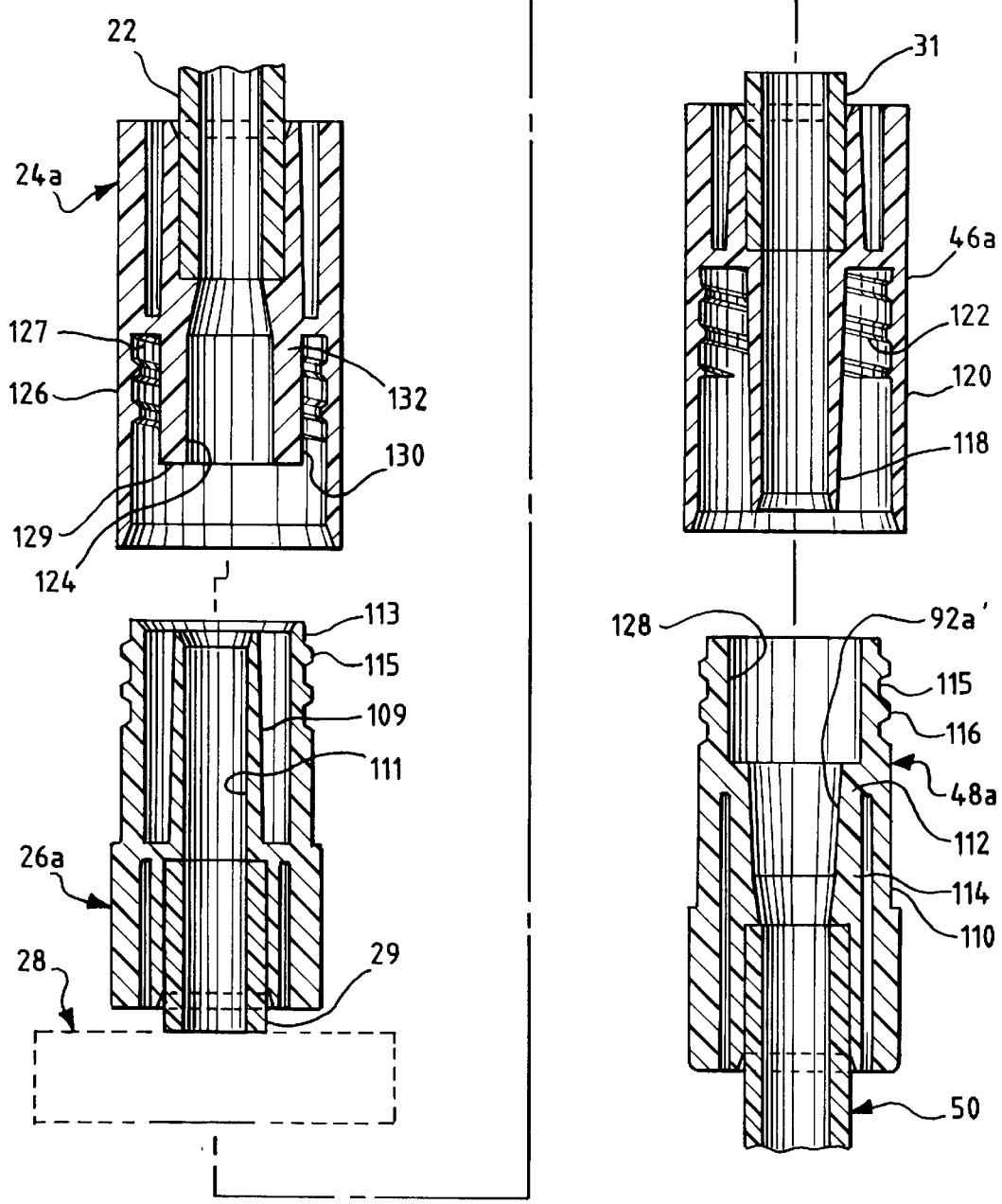
FIG. 6 is an enlarged, exploded longitudinal sectional view showing another embodiment of connectors as they may be joined together in the manner of FIG. 3.

Referring to FIG. 6, a preferred connector arrangement for the connectors of FIG. 3 is shown. In this embodiment, the reusable fifth patient connector 48a, corresponding to connector 48 of FIG. 1, can be seen to comprise a female tapered first sealing area 92a' corresponding in function to the threaded seal area 92a of FIG. 3. Connector 48a may carry an outer sleeve 110 surrounding most of the taper area and connected at an annular connection 112 with the structure 114 defining female taper surface 92a'. Outer sleeve 110 carries external threads 116.

The mating disposable connector 46a corresponds in function to connector 46 of FIG. 1, so that the respective two connectors 48a, 46a connect the second flexible tube 50 with the central assembly 28 of a blood set in accordance with this invention as specifically disclosed in FIG. 1. The design of connector 46a varies from connector 46. First sealing surface 118 comprises a male tapered sleeve. Outer sleeve 120 carries internal threads 122. Male taper surface 118 can seal with female luer surface 92a' of connector 48a. Outer sleeve 120 has internal threads 122 which engage threads 116 of connector 48a in locking relation.

Also, FIG. 6 can represent a detailed view of a preferred design for mating connectors 68, 70 in FIG. 1.

Also shown is a disposable third connector 26a which is similar in function and position to third connector 26 of FIG. 1 but with a different design. Male tapered sleeve 109 comprises the first sealing surface 111 mating with first sealing surface 124 of second connector 24a, which corresponds in function to connector 24 of FIG. 1. Thus, male tapered connector 26a seals at the respective first sealing surfaces 111, 124 at conical taper 124 of connector 24a. Sleeve 113 of third connector 26a carries threads 115 for engaging the threads 127 of connector 24a.

Thus it can be seen that four different connectors are used in this modification of FIG. 1 to permit central assembly 28 to be removed and replaced.

Figure 7:
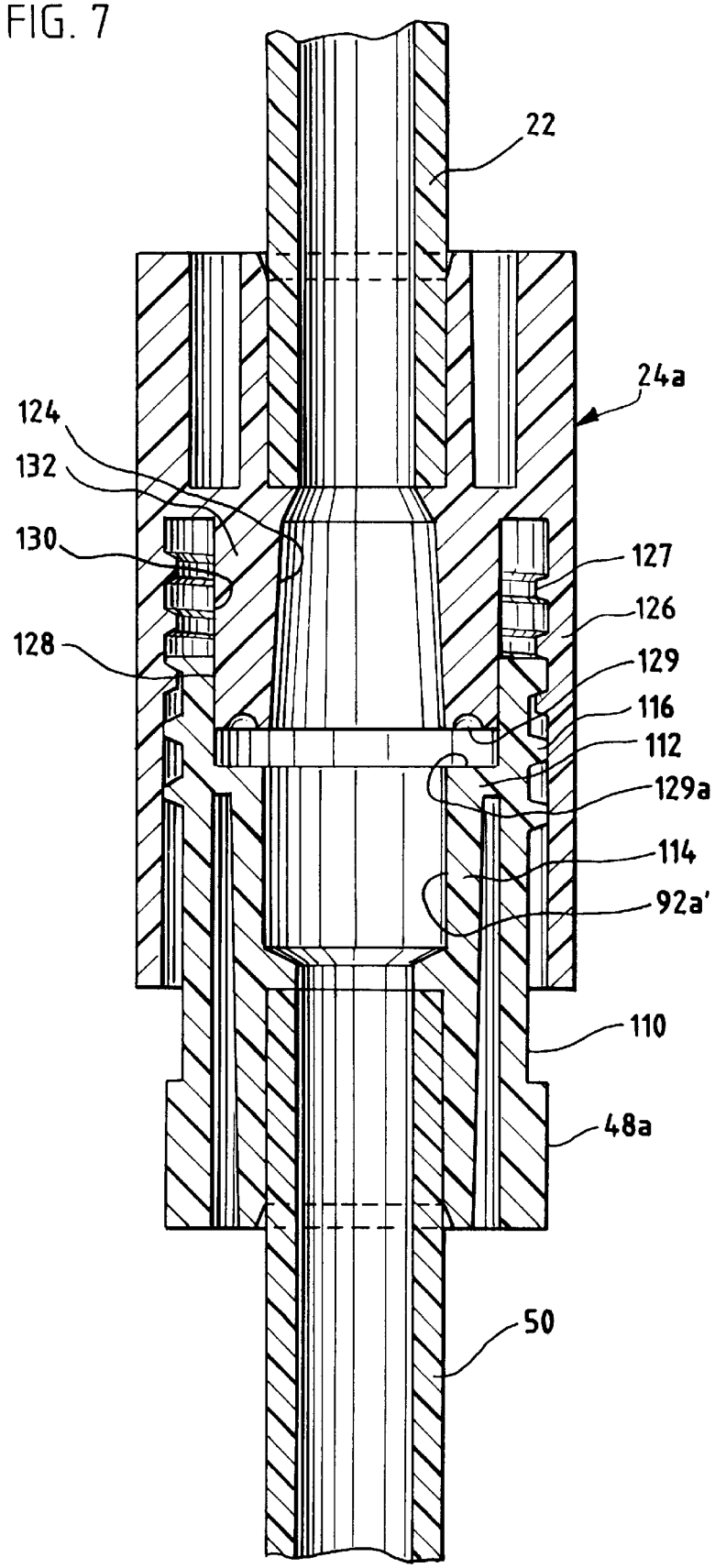
FIG. 7 is an enlarged, longitudinal sectional view showing another embodiment of connectors which are joined together for use in the configuration of FIG. 2.

Then, in accordance with this invention, when it is desired to remove a central assembly 28 from between the respective first and second conduits or flexible tubes for the purposes described above, connector 48a may be separated and then rejoined with connector 24a as in FIG. 7, to link together the respective first and second tubes 22, 50 of the device of FIG. 1.

As stated, connector 24a defines female taper surface 124, used as the first sealing surface for initial locking with a male connector 26a of central assembly 28 as in FIG. 1. Now, outer sleeve 126, having internal threads 127, locks with the external threads 116 of outer sleeve 110. At the same time, at least the distal end of outer sleeve 110 of connector 48a comprises a female taper surface 128 which engages with male tapered surface 130, which is defined by projecting member 132 of connector 24a. Thus projecting member 132 defines female taper surface 124 on the inside and a male taper surface 130 on its exterior, the latter including the respective second sealing area 130, 128 that provide the second seal between connectors 24a, 48a.

In this latter connection, the first luer taper areas 92a' and 124, as well as adjacent surfaces 129 and 129a, are exposed to fluid flow through the connectors and the respective tubes 22, 50 as shown in FIG. 7 for cleaning and antibacterial action. Accordingly, upon reuse of tubes 22, 50 by reconnection with another central assembly, the connectors 24a, 48a can form an aseptic seal in their respective first sealing areas 92a', 124.

Figure 8A:
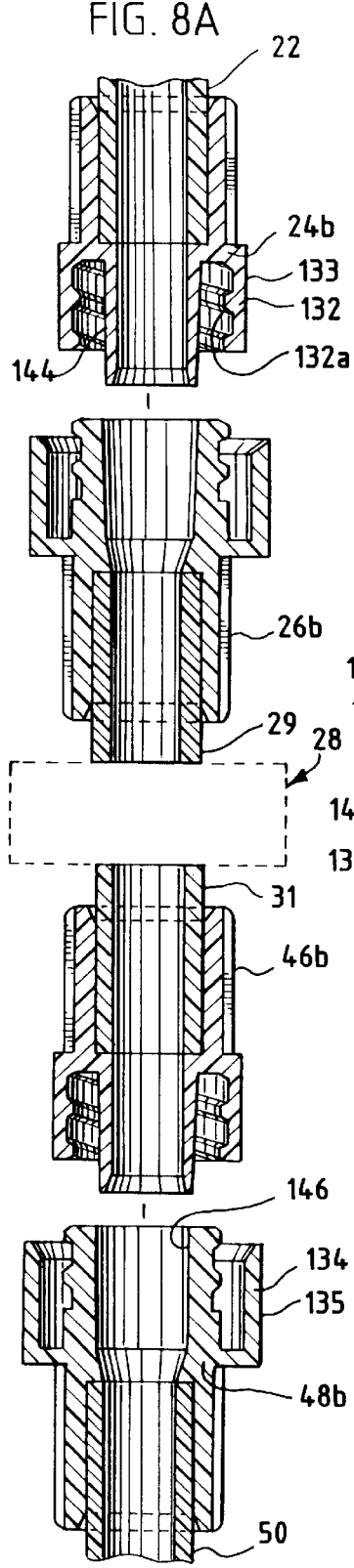
FIG. 8a is an enlarged, exploded longitudinal sectional view, showing another connector embodiment in the configuration of FIG. 1.

FIG. 8a shows a detailed modification of FIG. 1, in which the first tube 22 is terminated by connector 24b, which is shown to be a male luer lock-type connector capable of connecting with connector 26b in a manner analogous to the previously described connectors 24, 26.

Second tubing 50 connects with fourth connector 48b, which is a female-type luer lock connector and which connects with connector 46b in a manner similar to the previous connectors 46, 48.

Figure 8B:
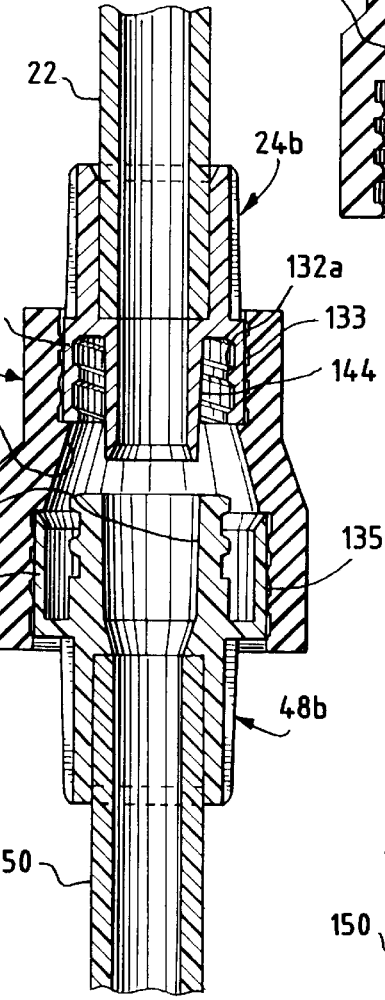
FIG. 8b is an enlarged longitudinal sectional view showing two connectors of FIG. 8a in the configuration of FIG. 2.

Then, in FIG. 8b, a detail from the situation of FIG. 2 is shown, where central assembly 28 and second and third connectors 26b, 46b have been removed, with connectors 24b, 48b being brought together in connected but spaced relationship by an overconnector 136. Each of connectors 24b, 48b respectively carry an integral locking ring 132 and sleeve 134. Connector 48b may be of the conventional design for a female luer connector but with this added, integral outer sleeve 134. Locking ring 132 has internal threads 132a, while sleeve 134 may be without threads.

It should be noted that the respective connectors 24b, 48b can engage each other in conventional luer lock relation. However, in the configuration shown in FIG. 8b they do not. Rather, overconnector 136 is provided, being of generally tubular form, to enclose and to retain the respective locking rings 132, 134 of the connectors in sealed, spaced relation as shown. Overconnector 136 may be made of a somewhat resilient material so that the respective connectors 24b, 48b may be each connected to it in snap-fit relation. Also, overconnector 136 defines an inner, annular spacing member 142 to provide inner spacing for connectors 24b, 48b by engagement of the sleeves 132, 134 with member 142.

The respective second seal area of connector 24b may comprise the outer surface 133 of sleeve 132, while the second seal of connector 48b comprises the outer surface 135 of sleeve 134. It can be seen that the first seal area for connector 24b is the conventional male luer taper surface 144, while the first sealing surface for connector 48b is the female luer taper surface 146.

One advantage of this system lies in the fact that only three different types of connectors need to be provided. Connector 26b can be seen to be of identical design to connector 48b, while connector 46b may be identical in design to connector 24b. This simplifies both the molding cost and the manufacture of the system, since the number of designs is reduced.

Figure 8C:
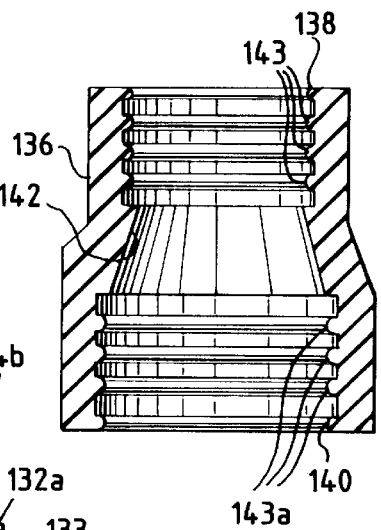
FIG. 8c is a longitudinal sectional view of an overconnector used in FIG. 8b.

The third connector, which is overconnector 36, is shown in FIG. 8c in its longitudinal cross section. Overconnector 136 may have optional end retaining members 138, 140, performing as snap-fit detents, which may be continuously annular or interrupted projections as desired, for retention of the respective connectors pressing inwardly against inner annular spacing member 142. Overconnector 136 may also be of differing end diameters as shown to accommodate the differently sized sleeves 132, 134. Also, overconnector 136 may carry integral sealing rings 143, 143a to press against the respective outer surfaces 133, 135 of sleeves 132, 134 to provide the desired second seal in the second sealing area.

Thus a sealed connection can be provided between the respective connectors 24b, 48b, by the use of overconnector 136, so that a sealed connection is provided without the use of the respective luer taper surfaces 144, 146 of the respective connectors. Rather, these surfaces 144, 146 are exposed to the flow of fluid through the respective flexible tubes 22, 50 so that these first sealing areas 144, 146 can be cleaned and exposed to antimicrobial activity. Thus they may be reused in an aseptic seal with a new central assembly 28.

Figure 8D:
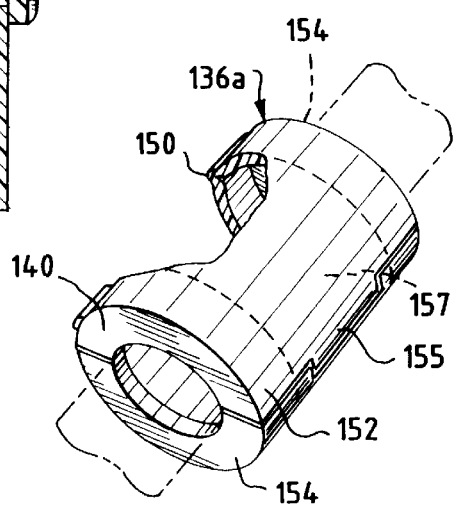
FIG. 8d is a perspective view, with portions broken away, of another embodiment of overconnector for use similar to the overconnector of FIG. 8c.

Referring to FIG. 8d, a perspective view of another overconnector 136a is shown. While it is shown to be tubular in nature, it may be molded of a single shot of plastic having a plastic living hinge 150 so that it forms two pivotable semicylindrical halves 152, 154 connected together by a conventional clasp 155. Retaining, annular endwalls 154 may be provided at each end, plus a central, inner ring 157 or the like to space the connectors in the overconnector. Thus, overconnector 136 may be applied laterally to the respective connectors 24b, 48b and snapped together to form the desired sealed connection for the processing phase of the set prior to reuse, per FIG. 2.

Alternatively, overconnector 136 may simply comprise an interference fit tube, optionally with inner, annular sealing member 142, to provide second seal areas 141, 143. Such a tube may be elastomeric, for example silicone or thermoplastic elastomer.

Figure 9:
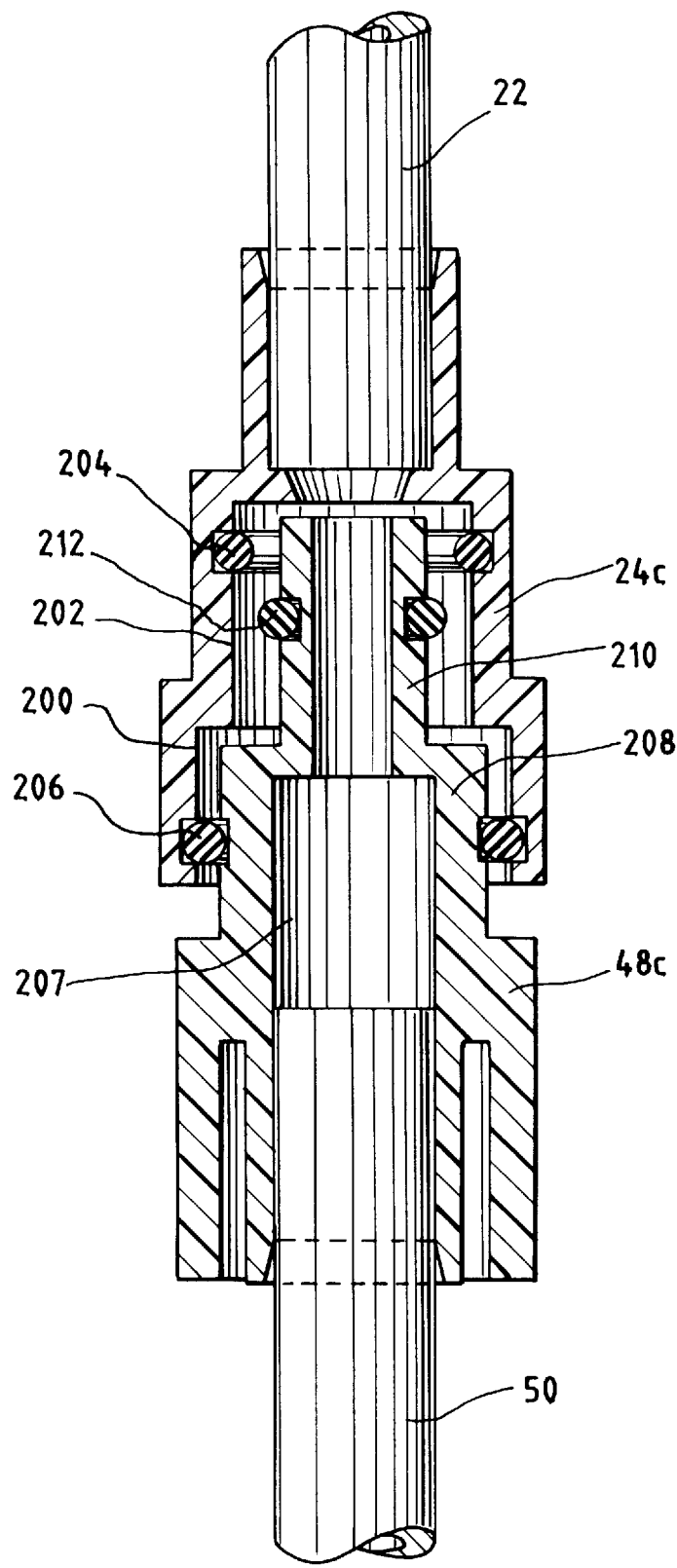
FIG. 9 is a longitudinal sectional view of another embodiment of joined connectors as shown in FIG. 2.

Referring to FIG. 9, another embodiment for the connectors shown in the connections of FIG. 2 is shown.

Connectors 24c, 48c may be used as replacements for connectors 24, 48, and also connectors 58, 70 as shown in FIG. 2. These connectors have been previously connected as correspondingly shown in FIG. 1 with other connectors which may be disposable. Now, the respective first and second tubes 22, 50 are brought together as in FIG. 2 for the purposes described above.

In this embodiment, connector 24c defines an aperture having a first, outer bore 200 of a diameter which is greater than inner bore 202 of the aperture shown. A first O-ring 204 is provided in the inner bore portion 202, while a second O-ring 206 is provided to the outer bore portion 200.

Connector 48c defines a lumen 207 extending through it, and a tubular projection having an inner portion 208 of a diameter that is greater than the diameter of an outer projection portion 210. Outer projection portion 210 carries another O-ring 212.

Alternatively, O-ring 206 may be carried on the first projection portion 208 rather than the inner surface of bore portion 200. The technology used with respect to the specific O-rings with respect to their securance and the materials of which they are formed may be conventional.

Thus, while connectors 24c and 48c may replace connectors 24, 48 (and connectors 58, 70) in the embodiment of FIG. 2, they are also capable of connecting with other connectors as indicated in the embodiment of FIG. 1 so that the desired central assembly may be placed between the respective connectors. The connectors of the central assembly may be proportioned to form a seal with the respective O-rings 204, 212, so that these seals define the respective first sealing areas (as previously discussed) for the connectors 24c, 48c. Then, when the central assembly is to be disconnected and removed, the respective connectors 24c, 48c may be brought together as shown in FIG. 9, with O-ring 206 comprising the second seal area (discussed previously) while the respective first O-rings 204, 212 are exposed as is desired for the first seal areas to contact with antiseptic solution passing through conduits 22, 50, to permit their restoration back into aseptic condition for reuse, along with tubes 22, 50.

Figure 10:
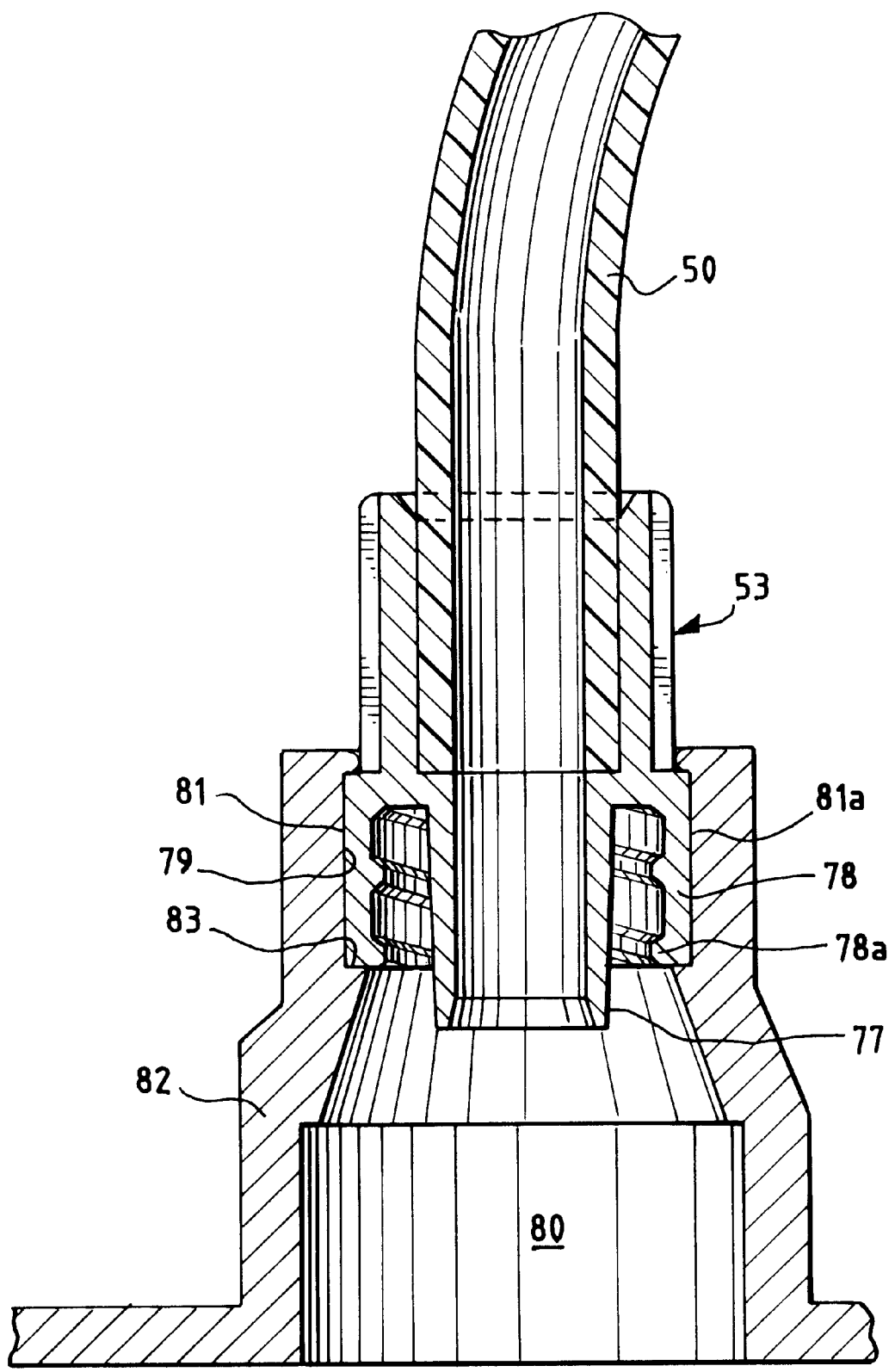
FIG. 10 is a sectional view of the connection of the patient connectors to the reuse machine as shown in FIG. 2.

Referring to FIG. 10, sixth connector 53 is shown in its connected relation with reuse port connector 82 which, in turn, is connected to the reuse apparatus 80 as shown in FIG. 2. The connection of sixth connector 76 with reuse port connector 84 may be of similar design.

After the extracorporeal circuit comprising tubes 50, 22, 56 and 72 and dialyzer 10 have been essentially cleared of blood, the central assemblies 28, 62 removed, and the respective tubes interconnected as previously discussed, the remaining set portion is connected to the reuse apparatus 80 for cleaning and preparation for storage, prior to reuse.

Reuse port 82 has a first annular sealing surface 81 and an annular stop 83.

Connector 53 defines a conventional first annular sealing surface 77 comprising a male taper, for use in its connection with a fistula needle set or the like while blood is being circulated through the system.

Connector 53 also carries a conventional sleeve 78 having locking threads 78a. The outer annular surface 79 of sleeve 78 may then serve as the second sealing surface in accordance with this invention, engaging with the annular sealing surface 81 of reuse port 82, for sealing engagement while in the configuration of FIGS. 2 and 10. Thus, as cleaning/disinfecting fluid passes from reuse device 80 through reuse connector 82 and sixth connector 53, the male taper first sealing area 77 may also be cleaned and disinfected prior to storage and reuse of the set.

Reuse port 82 may be somewhat flexible and resilient so that connector 53 can snap-fit into and out of recess 81a defined by connector 82 at the sealing surface area 81.

Figure 11:
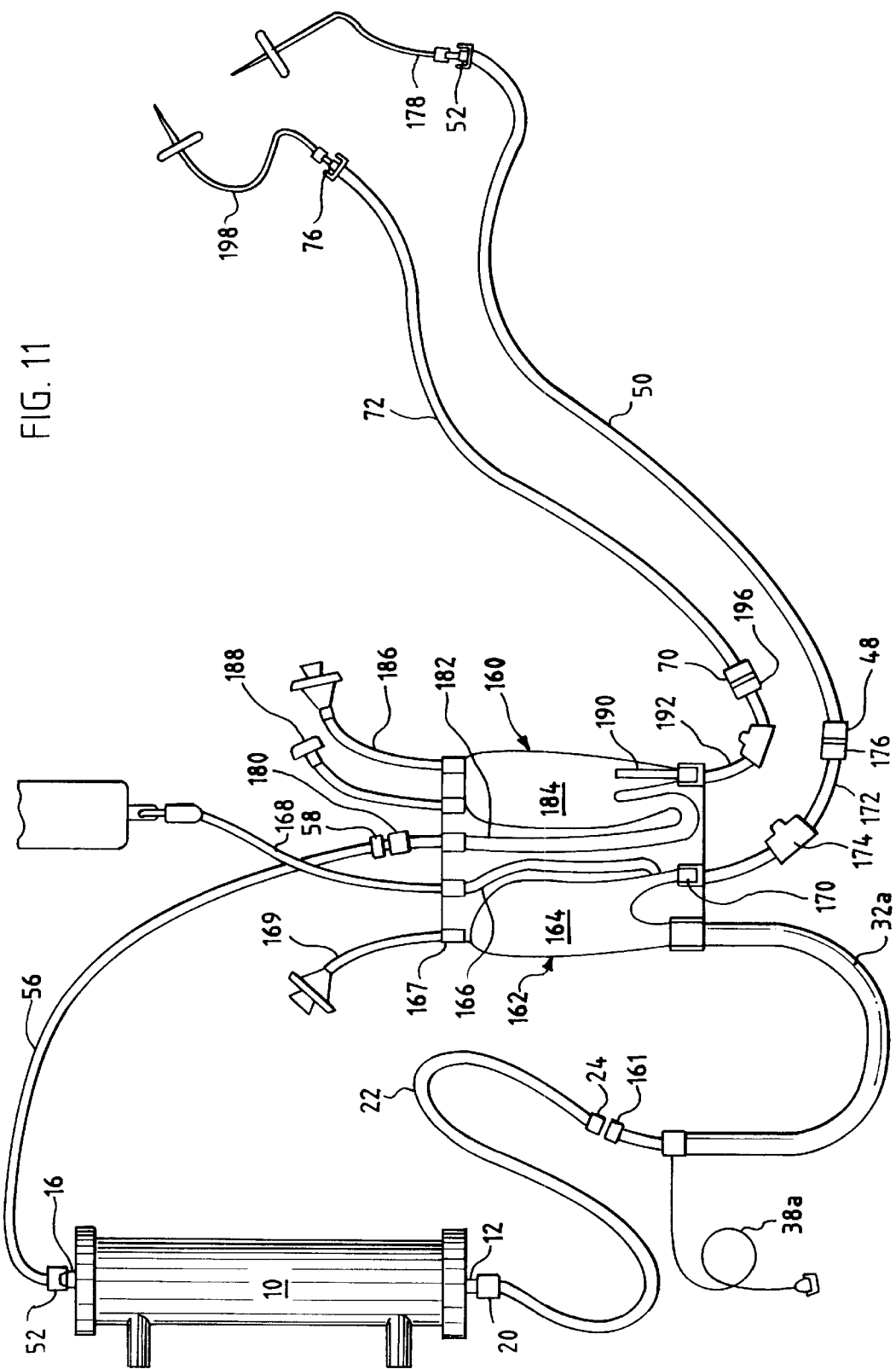
FIG. 11 is a plan view of another embodiment of a dialyzer connected to a combined arterial-venous blood set in another embodiment of this invention.

Referring to FIG. 11, a different embodiment of the blood conduits of a dialysis system in accordance with this invention is disclosed. As before, dialyzer 10 may be identical to the dialyzer of FIG. 1. The first tubing 22 of the arterial set may connect through first connector 20 to blood inlet 12 of the dialyzer. First tubing 22 may be identical to the tubing of FIG. 1, connecting by connector 24 to a different central assembly.

Specifically, central assembly 160 serves the function of both of the central assemblies of FIG. 1, with respective first and second lines 22, 50, 56, and 72 being connected thereto, the latter four blood lines being identical if desired to those of FIG. 1.

Connector 161 connects to roller pump tubing 32a of central assembly 160, with a branching heparin line 38a being provided if desired. Roller pump 32a connects to double chamber unit 162, typically made of a blow molded plastic parison, and being made of a substantially stiff plastic although more resilient material may be used if desired.

The blood from pump segment 32a passes into chamber 164. A branch connector line 166 is defined by structure 162 to connect to a saline line 168. A top port 167 permits connection to a transducer line 169. An outlet port 170 communicates with tubing 172 that carries an injection site 174 and outlet connector 176, which may correspond in structure and function to connector 46 of FIG. 1. Connector 176 may connect with fifth connector 48 of second flexible tubing 50, which may be identical to the corresponding second tube of FIG. 1. Second flexible tube 50 terminates in a sixth patient connector 52, shown to be connected to a fistula needle and tube 178 of conventional design. Thus the arterial set is shown.

Turning now to the venous side, blood outlet 16 of dialyzer 10 is connected to connector 52 of the first venous tubular portion 22, identical if desired with the corresponding structure of FIG. 1. First tube 56 terminates in second connector 58 as before, and communicates with third venous connector 180 of the structure, communicating with conduit 182 that leads to second chamber 184. Chamber 184 also has branch ports providing communication with the chamber for transducer protector line 186 and another line 188.

Chamber 184 has a bottom exit through filter 190 which may be integrally attached and of a design similar to that shown in U.S. Pat. No. 5,328,461. Bottom exit port communicates with tubing 192 which carries an injection site and fourth connector 196, which may be similar in structure and function to connector 68 of FIG. 1.

Connector 70 is carried by second venous tube 72, which may be identical to tube 72 of FIG. 1. Second venous tube 72 is terminated by a sixth connector 76, shown to be in communication with another fistula needle and tube 198.

Thus, this system may function in the manner similar to the arrangement of FIG. 1, using any of the connector designs shown herein and others as well, to provide dialysis to a patient, the blood access being through fistula sets 178, 198. At the termination of dialysis, as in the previous embodiment, connectors 24, 48 may be separated and connected to each other, while connectors 58, 70 may be similarly separated and connected to each other, so that the multiple chamber central assembly 162 is removed, and the system assumes the configuration of FIG. 2 for washing, sterilization, and storage until reuse is again desired of the dialyzer and tubing.

The above has been offered for illustrative purposes only, and is not intended to limit the scope of the invention of this application, which is as defined in the claims below.

That which is claimed:

1. A set for blood handing, which comprises:
    a first tube having ends which respectively carry a first connector and a second connector;
    a central assembly comprising a conduit having at least one of a blood degassing chamber, a connected branch tube, a pump device fitment, and an injection site, said central assembly carrying a third connector which is connected with said second connector, and a fourth connector;
    and a second tube having ends which respectively carry a fifth connector and a sixth connector, said fifth connector being connected to said fourth connector; at least said second and fifth connectors being of a type permitting repeated connection and disconnection to permit sealed blood flow through said set while said connectors are connected and in which said second connector and said fifth connector each define first sealing surfaces respectively positioned in sealing contact with other sealing surfaces of said third and fourth connectors; said second and fifth connectors each also having second sealing surfaces and being also connectable with each other to form a sealed connection by contact of said second sealing surfaces while said first sealing surfaces are positioned in exposed manner within the connected second and fifth connectors, so that antimicrobial solution in said joined first and second tubes can be in contact with said first sealing surfaces.

2. The set of claim 1 in which said second and fifth connectors each define a threaded sleeve of differing diameter from the other sleeve to permit telescoping, threaded interengagement for locking connection while said second sealing surfaces are in sealing contact.

3. The set of claim 2 in which the threaded sleeve of at least one of said second and fifth connectors is threaded both inside and out.

4. The set of claim 2 in which at least one of said first and second tubes are free of lateral branching connections.

5. The set of claim 1 in which at least one of said first and second tubes are free of lateral branching connections.

6. The set of claim 1 in which said first sealing surfaces are defined by first O-rings and the second sealing surfaces are defined by second O-rings.

7. A flow-through blood treatment device and a connected blood set portion which comprises:

a housing, a blood inlet, a blood outlet, and at least one membrane in the housing, said housing defining a blood flow path between said blood inlet and outlet on one side of the membrane and a second flow path defined on the other side of the membrane, said blood inlet and said blood outlet being each respectively connected to lengths of first blood flow tubes at first connection sites positioned at one end of each of said respective lengths of first blood flow tubes, each first tube carrying on its other end a second connector which is connected to a fifth connector carried on one end of a second blood flow tube, each length of second tube being connected to a sixth connector on its end opposed to the end which carries the fifth connector, each of said sixth connectors being connected to a respective inlet and flow outlet of reuse equipment for passing cleaning and storage solution through the blood treatment device and connected tubes.

8. A flow-through blood treatment device and connected set portion of claim 7 in which the housing of said flow-through blood treatment device is part of a hemodialyzer and at least one of said first and second tubes is permanently connected to at least one of said blood inlet and blood outlet.

9. The flow-through blood treatment device and connected set portion of claim 7 in which each of said sixth connectors is secured to a reuse connector as part of said reuse equipment, each of said sixth connectors defining a first sealing surface for sealing contact with a sealing surface of a patient connector for receiving and conveying blood from and to a patient while circulating blood through said blood treatment device, said reuse connectors holding said sixth connectors in a position causing said first sealing surfaces of the sixth connectors to be exposed within the joined connector interior so that antimicrobial solution can be in contact with said first sealing surfaces.

10. The flow-through blood treatment device and connected set portion of claim 7 in which at least one of said first and second blood flow tubes are free of lateral branching connections.

11. The set of claim 7 in which said second connector and said fifth connector each have first sealing surfaces, said second and fifth connectors each also having second sealing surfaces, said second and fifth connectors being also connectable with each other to form a sealed connection by contact of said second sealing surfaces while said first sealing surfaces are positioned in exposed manner within the connected second and fifth connectors, so that antimicrobial solution in said joined first and second tubes can be in contact with said first sealing surfaces.

12. The set of claim 11 in which said second and fifth connectors each define a threaded sleeve of differing diameter from the other threaded sleeve to permit telescoping, threaded interengagement for locking connection, with said second sealing surfaces being in sealing contact with each other.

13. The set of claim 12 in which the threaded sleeve of at least one of said second and fifth connectors is threaded both inside and out.

14. The set of claim 11 in which said first sealing surfaces are defined by first O-rings and the second sealing surfaces are defined by at least one second O-ring.

15. The set of claim 11 in which an overconnector connects said second and fifth connectors in sealed relation to each other while permitting fluid flow through said connectors, in which the first sealing surface of each said second and fifth connectors is spaced from the other first sealing surface and positioned in internally exposed manner while in connected relation with said overconnector so that antimicrobial solution in the joined connectors can be in contact with said first sealing surfaces.

16. A flow-through blood treatment device and a connected blood set portion which comprises:

a housing, a blood inlet, a blood outlet, and at least one membrane in the housing, said housing defining a blood flow path between said blood inlet and outlet on one side of the membrane and a second flow path defined on the other side of the membrane, said blood inlet and said blood outlet being each respectively connected to lengths of first blood flow tubing at first connection sites positioned at one end of each of said respective lengths of said first blood flow tubing, each first tubing carrying on its other end a second connector which is connected to a fifth connector carried on one end of a second flexible blood tube, each length of second flexible blood tube being connected to a sixth connector opposed to the second tube end that carries the fifth connector, and in which each of said second flexible tubes are connected by said sixth connectors to reuse equipment for passing cleaning/storage solution through the device and connected tubes, at least one of said first and second flexible tubes being free of lateral branching connections.

17. The set of claim 16 in which said second connector and said fifth connector each have first sealing surfaces, said second and fifth connectors each also having second sealing surfaces, said second and fifth connectors being also connectable with each other to form a sealed connection by sealing contact of said second sealing surfaces while said first sealing surfaces are positioned in exposed manner within the connected second and fifth connectors, so that antimicrobial solution in said joined first and second flexible tubes can be in contact with said first sealing surfaces.

18. The set of claim 17 in which said second and fifth connectors each define a threaded sleeve of differing diameter from the other threaded sleeve to permit telescoping, threaded interengagement for locking connection while said second sealing surfaces are in sealing contact with each other.

19. The set of claim 17 in which the threaded sleeve of at least one of said second and fifth connectors is threaded both inside and out.

20. The set of claim 17 in which said first blood flow tubing is permanently connected to said housing at said first connection site.

21. The flow-through blood treatment device and connected set portion of claim 17 in which the housing of said flow-through blood treatment device is part of a hemodialyzer.

22. The set of claim 17 in which said first sealing surfaces are defined by first O-rings and the second sealing surfaces are defined by second O-rings.

23. The set of claim 17 in which an overconnector connects said second and fifth connectors in sealed relation to each other while permitting fluid flow through said connectors, in which the first sealing surface of each said second and fifth connectors is spaced from the other first sealing surface and positioned in internally exposed manner while in connected relation with said overconnector so that antimicrobial solution in the joined connectors can be in contact with said first sealing surfaces.

24. A combined arterial and venous set for blood handling, which comprises:
- a first tube having ends which respectively carry a first connector for connection which a source of blood, and a second connector;
- a central assembly which comprises first and second blood degassing chambers connected together in an integral piece, plus a pump device fitment, said central assembly carrying a third connector which is connected with said second connector, and a fourth connector, said third and fourth connectors being in fluid flow connection with the first blood degassing chamber;
- a second tube having ends which respectively carry a fifth connector and a sixth connector, said fifth connector being connected to said fourth connector, at least said first, second, fifth and sixth connectors all being of a type permitting repeated connection and disconnection to permit sealed blood flow through said set;
- said second tube being connected to a flow-through blood treatment device which comprises a housing, a blood inlet, a blood outlet, and at least one membrane in the housing, said housing defining a blood flow path between said blood inlet and outlet, said sixth connector connecting to said blood inlet of the blood treatment device;
- a third tube having ends which respectively carry a seventh connector and an eighth connector, said seventh connector being connected to said blood outlet of a blood treatment device, said eighth connector communicating with the second blood degassing chamber of the central assembly; a fourth tube having ends which respectively carry a ninth connector and a tenth connector, said ninth connector being connected to the second chamber of said central assembly to receive blood through said chamber from the third flexible tube, at least said seventh, eighth, ninth, and tenth connectors all being of the type permitting repeated connection and disconnections to permit sealed blood flow through said set while said connectors are connected, said seventh connector being also capable of connection with said eighth connector and said second connector being connectable with said fifth connector, to permit said first and second flexible tubes to be connected together and said third and fourth tubes to connected together apart from the presence of said central assembly.

25. The set for blood handling of claim 24 in which said flow-through blood treatment device is a hemodialyzer.

26. The set of claim 24 in which said pump device fitment comprises tubing for a roller pump, said fourth connector being carried on tubing adjacent one end of said roller pump tubing.

27. A tubular set for blood handling which comprises an overconnector, a first tube which carries one connector and a second tube which carries another connector, said connectors respectively defining a first sealing surface that provides sealing contact with a sealing surface of another connector when in connected relation, said overconnector connecting said connectors in sealed relation to each other while permitting fluid flow through said connectors, in which the first sealing surface of each of said connectors is spaced from the other first sealing surface and positioned in internally exposed manner in connected relation with said overconnector so that antimicrobial solution in the joined connectors can be in contact with said first sealing surfaces, said overconnector comprising a substantially tubular member which encloses and spaces said connectors from each other, said overconnector comprising an annular, inwardly projecting, central seal member to provide spacing and an abutment seal between the connectors.

28. The tubular set of claim 27 in which said overconnector comprises a pair of hingedly connected, semicylindrical members which pivot together in the form of a "clam shell" to seal and to space said connectors.

29. A blood treatment device and a set for blood handling, which comprises;
- a blood treatment device;
- a first flexible tube having an end connected at a first connection site to one of a blood inlet or blood outlet of said blood treatment device, said device defining a blood flow path between said blood inlet and outlet, said first tube having a second connector at its end opposed to said first connection site;
- a second flexible tube having ends which respectively carry a fifth connector and a sixth connector, said fifth connector being indirectly connected to said second connector of the first flexible tube by mutual connection to a central assembly, said central assembly comprising a blood flow path extending through at least one of a degassing chamber and a pump device fitment, said second, fifth, and sixth connectors being all of the type permitting repeated connection and disconnection, said second and fifth connectors being also capable of direct sealing connection with each other.

30. The blood handling set of claim 29 in which said first and second tubes define lumens having a cross-sectional area of about 0.17 to 0.4 cm$^2$.

31. A set for blood handling, which comprises:
- a first conduit having ends which respectively carry a first connector and a second connector;
- a central assembly comprising another conduit having at least one of a blood degassing chamber, a connected branch tube, a pump device fitment, and an injection site, said central assembly carrying a third connector which is connected with said second connector, and a fourth connector; and
- a second conduit having ends which respectively carry a fifth connector and a sixth connector, said fifth connector being connected to said fourth connector; at least said second and fifth connectors being of a type permitting repeated connection and disconnection to permit sealed blood flow through said set while said connectors are connected and in which said second connector and said fifth connector each define first sealing surfaces respectively positioned in sealing contact with other sealing surfaces of said third and fourth connectors, said second and fifth connectors each also having second sealing surfaces and being also connectable with each other to form a sealed connection by contact of said second sealing surfaces while said first sealing surfaces are positioned in exposed manner within the connected second and fifth connectors, so that antimicrobial solution in said joined first and second conduits can be in contact with said first sealing surfaces.

* * * * *